(12) United States Patent
Schon et al.

(10) Patent No.: US 7,018,374 B2
(45) Date of Patent: Mar. 28, 2006

(54) SPLITTABLE MULTILUMEN CATHETER ASSEMBLY

(75) Inventors: Donald A. Schon, Paradise Valley, AZ (US); Anthony J. Madison, Lansdale, PA (US); Timothy M. Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 258 days.

(21) Appl. No.: 10/659,824

(22) Filed: Sep. 11, 2003

(65) Prior Publication Data

US 2004/0054321 A1 Mar. 18, 2004

Related U.S. Application Data

(63) Continuation of application No. 10/300,999, filed on Nov. 21, 2002, now Pat. No. 6,695,832, which is a continuation-in-part of application No. 09/585,149, filed on Jun. 1, 2000, now Pat. No. 6,717,749.

(60) Provisional application No. 60/331,882, filed on Nov. 21, 2001.

(51) Int. Cl.
*A61M 27/00* (2006.01)

(52) U.S. Cl. ..................... 604/544; 606/540
(58) Field of Classification Search ............. 606/544, 606/540, 541, 542, 543, 8, 175, 264
See application file for complete search history.

(56) References Cited

U.S. PATENT DOCUMENTS

| 701,075 A | 5/1902 | McCully |
| 2,286,462 A | 6/1942 | Chaffin |
| 3,144,868 A | 8/1964 | Jascalevich |

(Continued)

FOREIGN PATENT DOCUMENTS

| BE | 0834211 | 2/1978 |
| CA | 1092927 | 1/1981 |
| CA | 1193508 | 9/1985 |
| EP | 0386408 | 9/1990 |
| FR | 1285953 | 12/1962 |

OTHER PUBLICATIONS 11.0 French Uldall Double Lumen Hemodialysis Catheter Tray sheet (date unknown).
Sheet listing three references, dated 1999.
International Search Report Mailed Jun. 4, 2003.
Brochure entitled, "Schon Cath", (One Dual Catheter) permanent access, Jul. 1996, 2 pages.
Brochure entitled, "The MedComp TESIO Catheter", *MEDCOMP, Harleysville, PA*, date unknown, 4 pages.
Canaud, B., et al., "Internal Jugular Vein Cannulation with two silicone rubber catheters", *Artificial Organs*, 1986, 10(5), 397–403.

(Continued)

*Primary Examiner*—Daniel Robinson
(74) *Attorney, Agent, or Firm*—Joseph E. Maenner; Monte & McGraw, P.C.

(57) ABSTRACT

A multilumen catheter assembly is provided, which includes a unitary portion and at least two distal end tubes extending distally from the unitary portion. The unitary portion includes an exterior having a generally round or oval shape in cross section and includes at least two distal end tubes of generally circular (or other) cross sectional shape extending longitudinally therethrough. The catheter assembly may be made by extruding a unitary tube having internal longitudinally extending lumens (of circular or other shape), then splitting the tube on its distal end portion to form distal end tubes. The tubes are then ground and polished, the finished tubes retaining in combination the generally oval cross sectional shape of the unitary extrusion, or the finished tubes can each be finished to a circular, or other, cross sectional shape; or the finished tubes could include a combination of cross sectional shapes over its longitudinal length.

14 Claims, 10 Drawing Sheets

U.S. PATENT DOCUMENTS

| | | |
|---|---|---|
| 3,359,974 A | 12/1967 | Khalil |
| 3,400,714 A | 9/1968 | Sheridan |
| 3,804,097 A | 4/1974 | Rudie |
| 3,823,720 A | 7/1974 | Tribble |
| 3,863,632 A | 2/1975 | Schwartz |
| 4,072,146 A | 2/1978 | Howes |
| 4,098,275 A | 7/1978 | Consalvo |
| 4,134,402 A | 1/1979 | Mahurkar |
| 4,203,436 A | 5/1980 | Grimsrud |
| 4,385,631 A | 5/1983 | Uthmann |
| 4,402,683 A | 9/1983 | Kopman |
| 4,405,313 A | 9/1983 | Sisley et al. |
| 4,427,012 A | 1/1984 | Miller |
| D272,651 S | 2/1984 | Mahurkar |
| 4,432,752 A | 2/1984 | Marlon |
| 4,451,252 A | 5/1984 | Martin |
| 4,493,696 A | 1/1985 | Uldall |
| 4,548,597 A | 10/1985 | Nelson |
| 4,568,329 A | 2/1986 | Mahurkar |
| 4,583,968 A | 4/1986 | Mahurkar |
| 4,619,643 A | 10/1986 | Bai |
| 4,623,327 A | 11/1986 | Mahurkar |
| 4,654,032 A | 3/1987 | Morales-George |
| 4,682,978 A | 7/1987 | Martin |
| 4,692,141 A | 9/1987 | Mahurkar |
| 4,770,652 A | 9/1988 | Mahurkar |
| 4,808,155 A | 2/1989 | Mahurkar |
| 4,842,582 A | 6/1989 | Mahurkar |
| 4,895,561 A | 1/1990 | Mahurkar |
| 4,898,669 A | 2/1990 | Tesio |
| 4,925,452 A | 5/1990 | Melinyshyn et al. |
| 5,053,004 A | 10/1991 | Markel et al. |
| 5,053,023 A | 10/1991 | Martin |
| 5,057,075 A | 10/1991 | Moncrief et al. |
| 5,059,170 A | 10/1991 | Cameron |
| 5,084,013 A | 1/1992 | Takase |
| 5,100,395 A | 3/1992 | Rosenberg |
| 5,106,386 A | 4/1992 | Isner et al. |
| 5,107,856 A | 4/1992 | Kristiansen et al. |
| 5,156,592 A | 10/1992 | Martin et al. |
| 5,167,220 A | 12/1992 | Brown |
| 5,171,216 A | 12/1992 | Dasse et al. |
| 5,197,951 A | 3/1993 | Mahurkar |
| 5,209,723 A | 5/1993 | Twardowski et al. |
| 5,221,255 A | 6/1993 | Mahurkar et al. |
| 5,221,256 A | 6/1993 | Mahurkar |
| 5,236,016 A | 8/1993 | Vogelsang |
| 5,318,517 A | 6/1994 | Reiman |
| 5,334,167 A | 8/1994 | Cocanower |
| 5,336,220 A | 8/1994 | Ryan et al. |
| 5,338,308 A | 8/1994 | Wilk |
| 5,346,471 A | 9/1994 | Raulerson |
| 5,350,358 A | 9/1994 | Martin |
| 5,374,245 A | 12/1994 | Mahurkar |
| 5,378,230 A | 1/1995 | Mahurkar |
| 5,378,241 A | 1/1995 | Haindl |
| 5,380,276 A | 1/1995 | Miller et al. |
| 5,385,548 A | 1/1995 | Williams et al. |
| 5,405,341 A | 4/1995 | Martin |
| 5,480,380 A | 1/1996 | Martin |
| 5,549,579 A | 8/1996 | Batdorf et al. |
| 5,562,618 A | 10/1996 | Cai et al. |
| 5,599,304 A | 2/1997 | Shaari |
| 5,624,413 A | 4/1997 | Markel et al. |
| 5,683,640 A | 11/1997 | Miller et al. |
| 5,718,692 A | 2/1998 | Schon et al. |
| 5,776,111 A | 7/1998 | Tesio |
| 5,785,686 A | 7/1998 | Runge |
| 5,800,414 A | 9/1998 | Cazal |
| 5,807,311 A | 9/1998 | Palestrant |
| 5,947,953 A | 9/1999 | Ash et al. |
| 6,001,079 A | 12/1999 | Pourchez |
| 6,074,374 A | 6/2000 | Fulton |
| 6,190,349 B1 | 2/2001 | Ash et al. |
| 6,309,379 B1 * | 10/2001 | Willard et al. ............... 600/467 |
| 6,379,346 B1 * | 4/2002 | McIvor et al. ............... 604/524 |
| 6,656,166 B1 * | 12/2003 | Lurie et al. .................. 604/264 |
| 6,692,464 B1 * | 2/2004 | Graf ........................... 604/160 |
| 6,719,749 B1 * | 4/2004 | Schweikert et al. ......... 604/544 |
| 6,758,854 B1 * | 7/2004 | Butler et al. ................. 606/194 |

OTHER PUBLICATIONS

Hocken, A.G., "Percutaneous femoral vein catheterization for hemodialysis: a single needle technique", *Clinical Nephrology*, 2979, 12(2), 93–94.

Tesio, F. et al., "Double catheterization of the internal jugular vein for hemodialysis: indications, techniques and results", *Artificial Organs*, 1994, 18(4), 301–304.

* cited by examiner

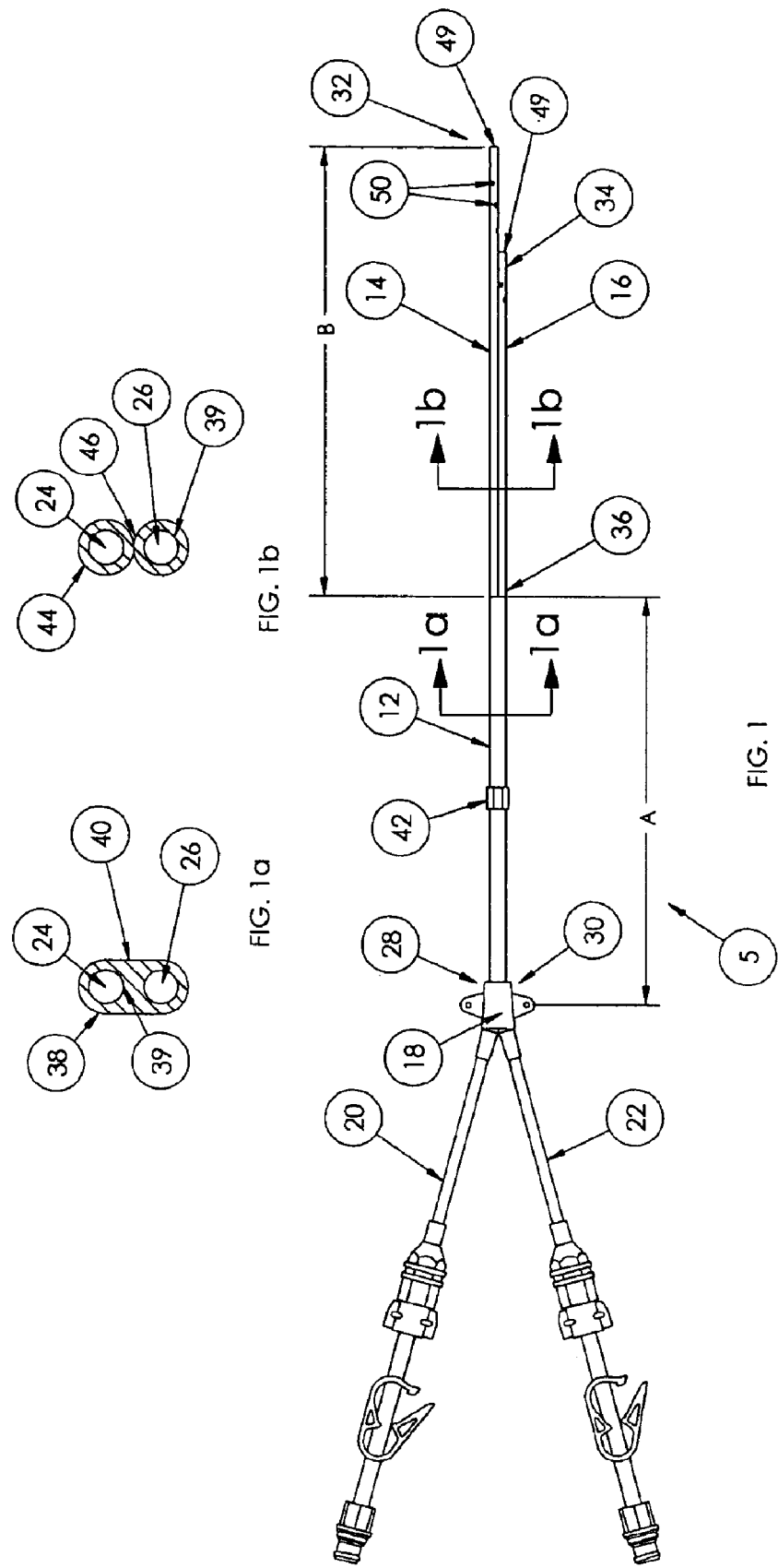

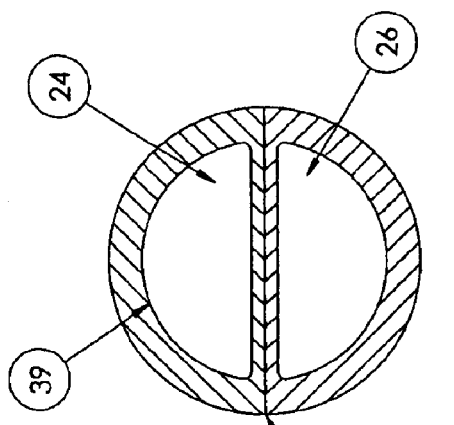
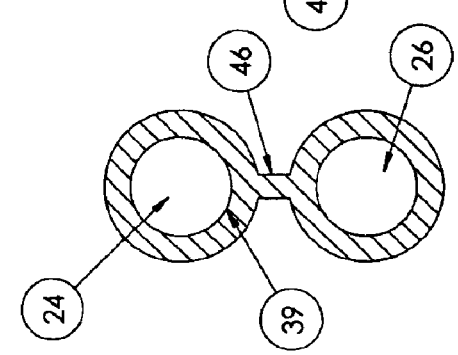
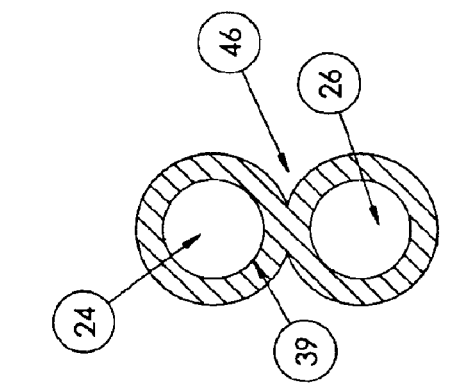
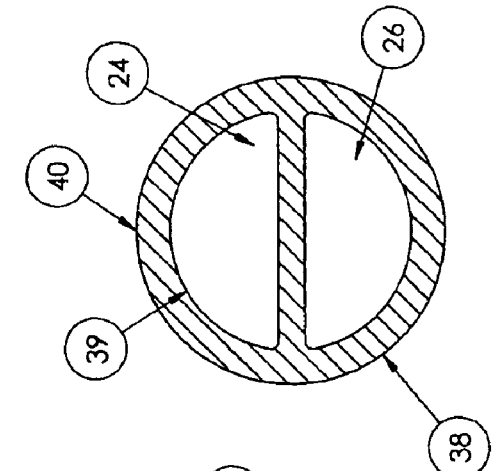
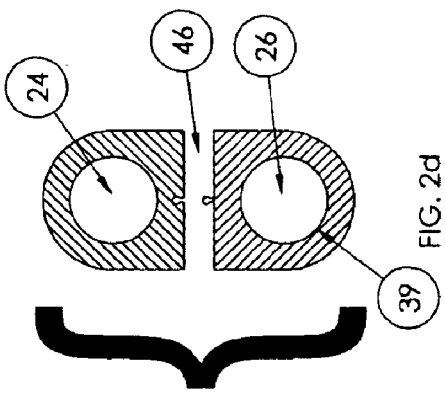

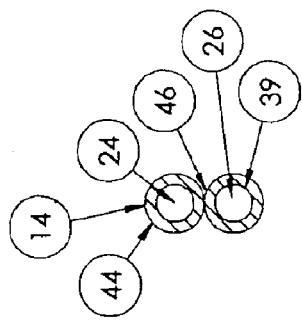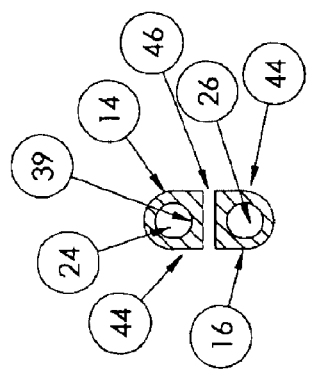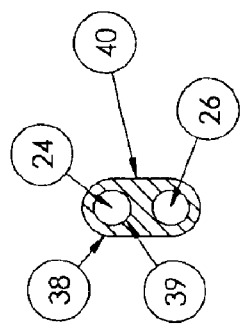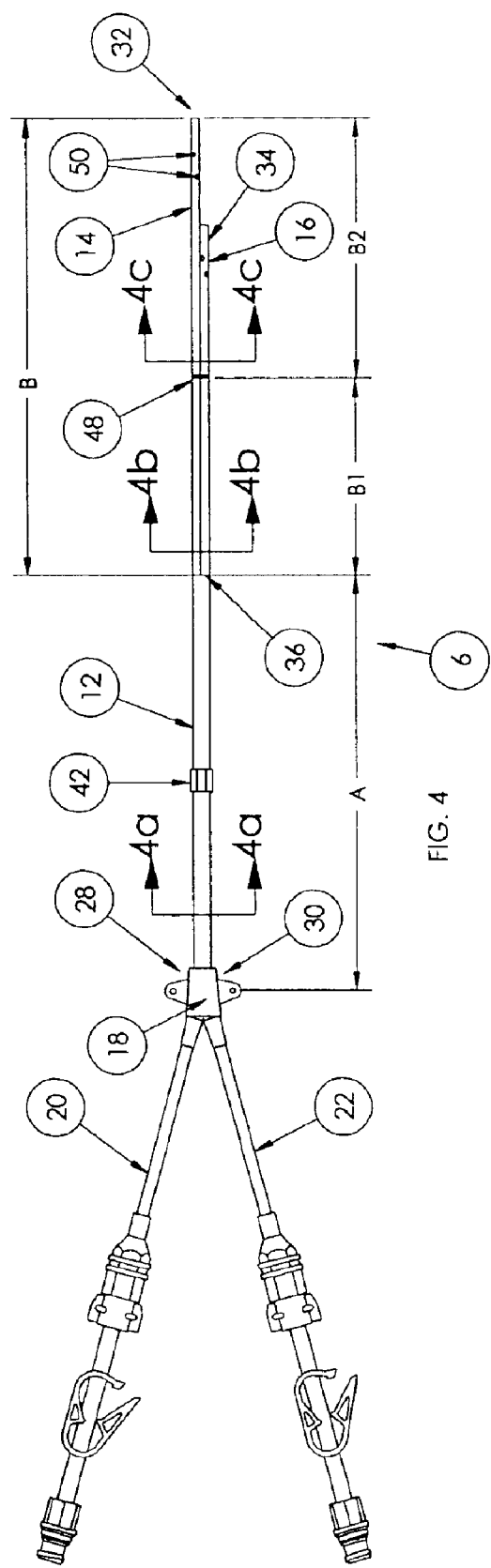

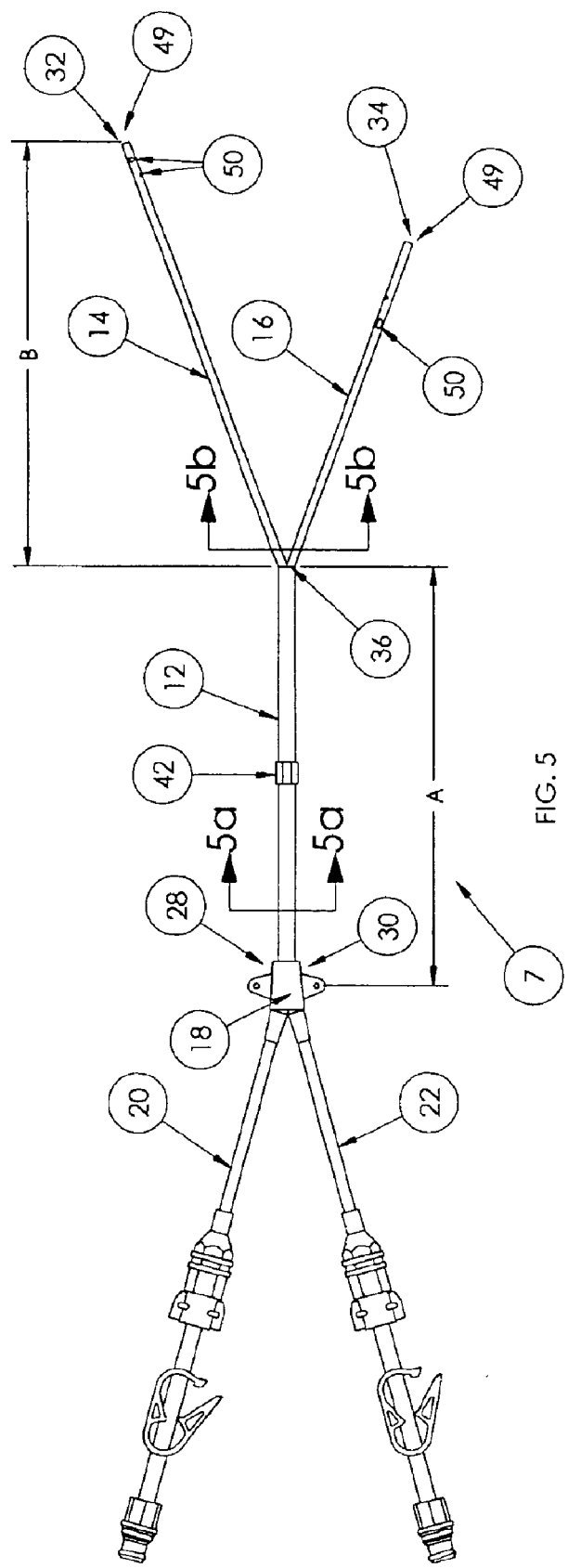
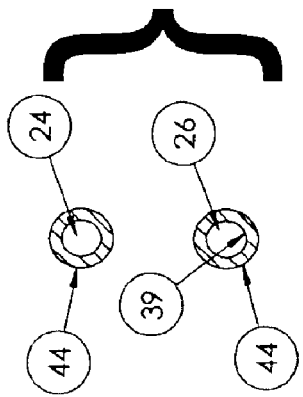
FIG. 5b
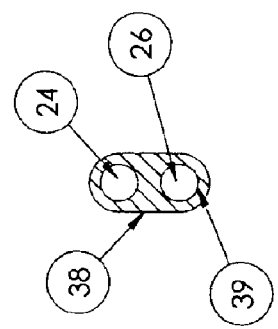
FIG. 5a
FIG. 5

FIG. 6b
FIG. 6a
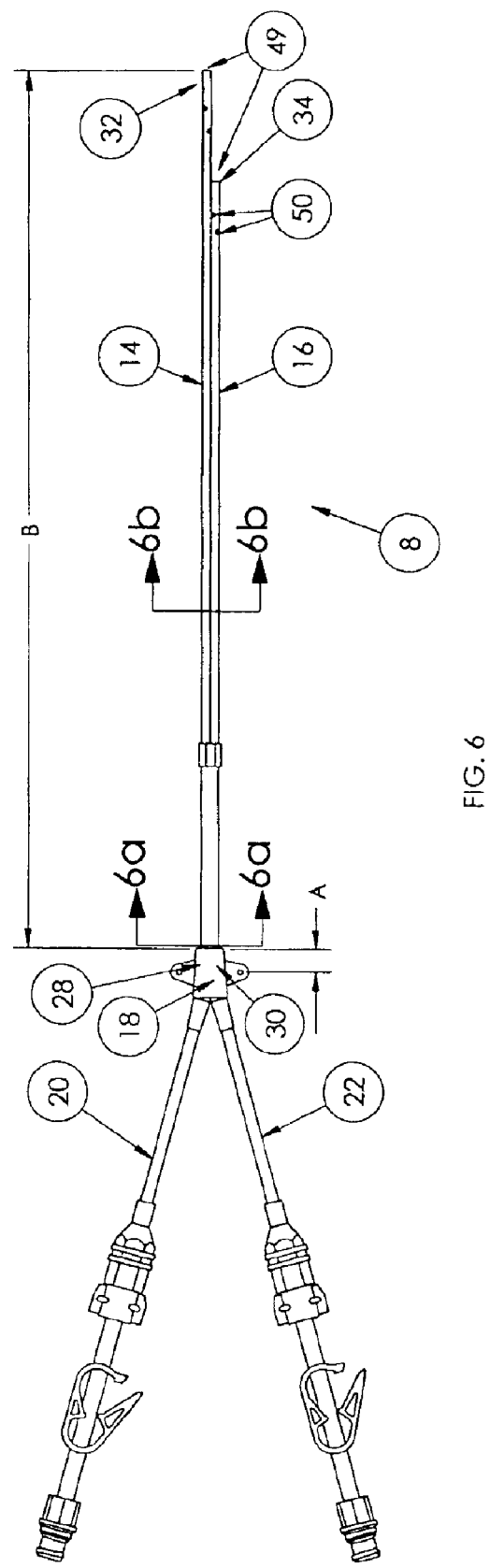
FIG. 6

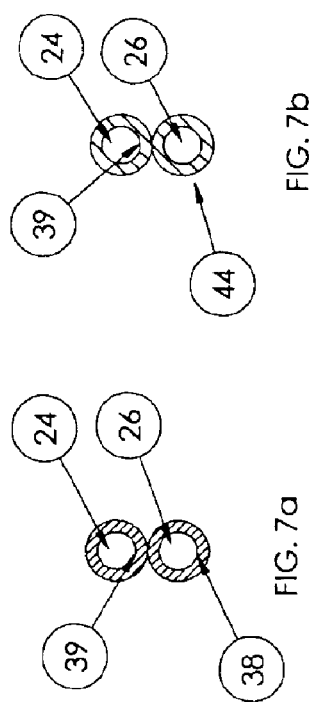
FIG. 7b
FIG. 7a
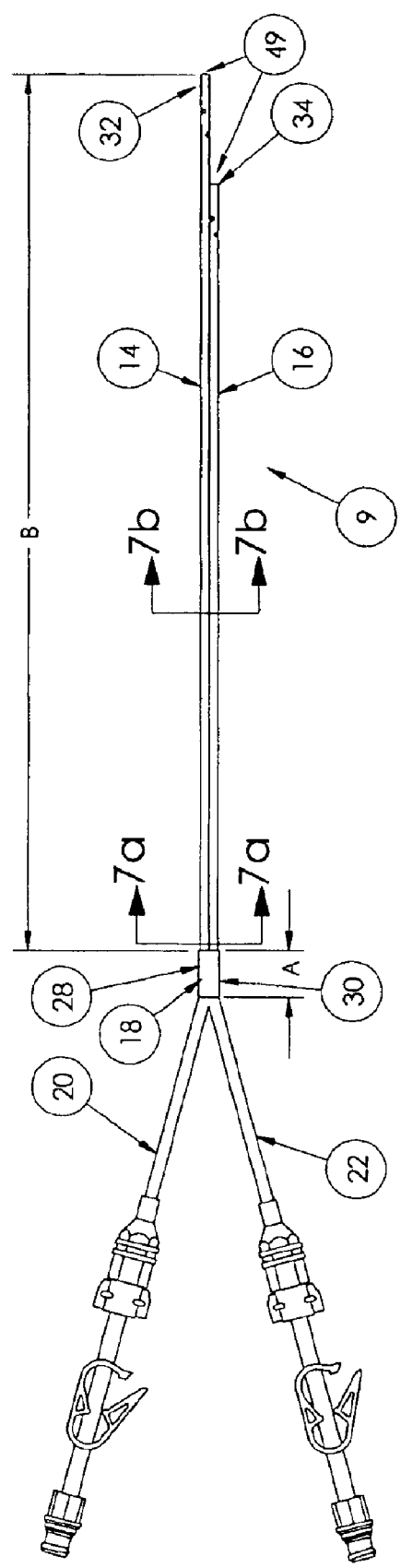
FIG. 7

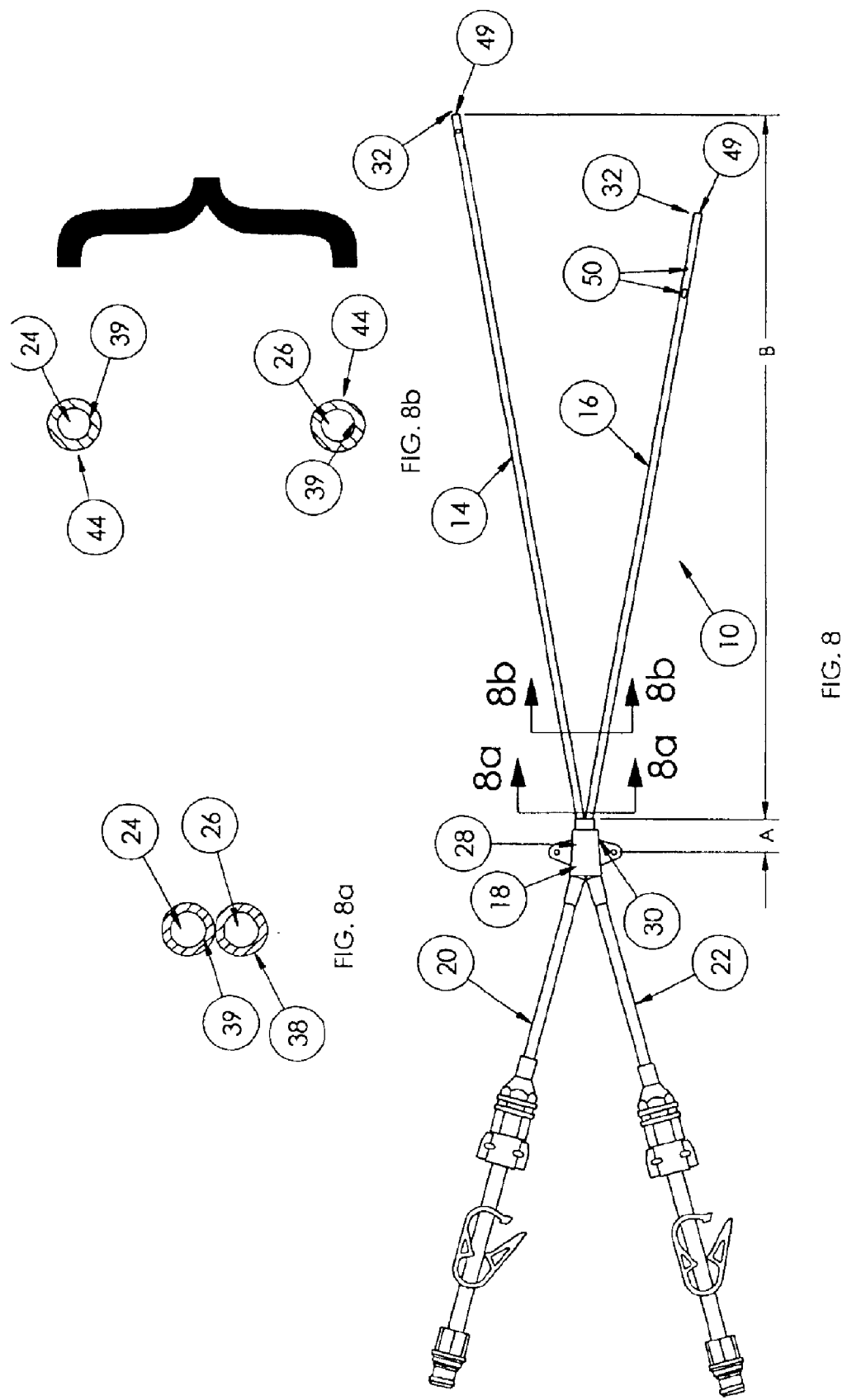

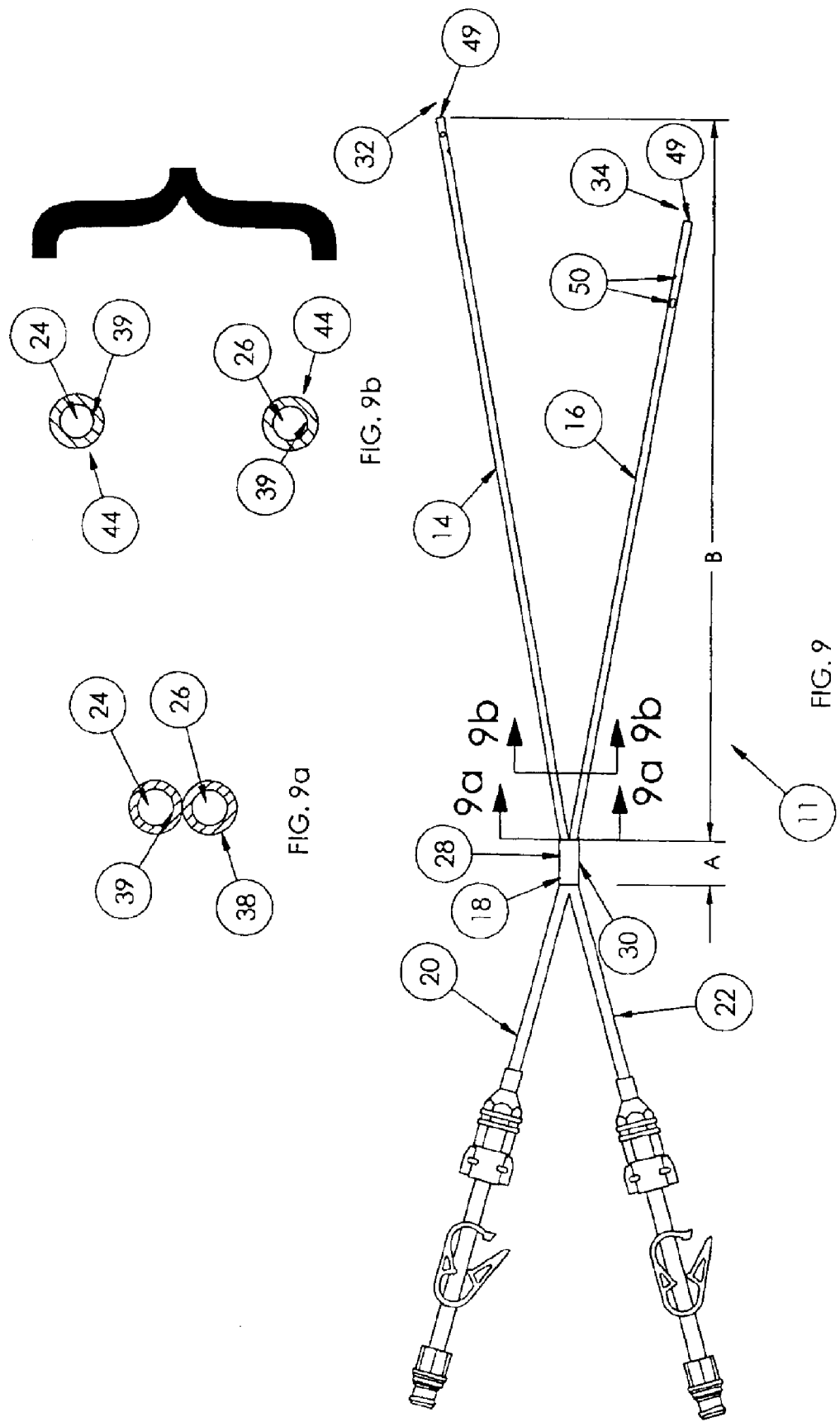

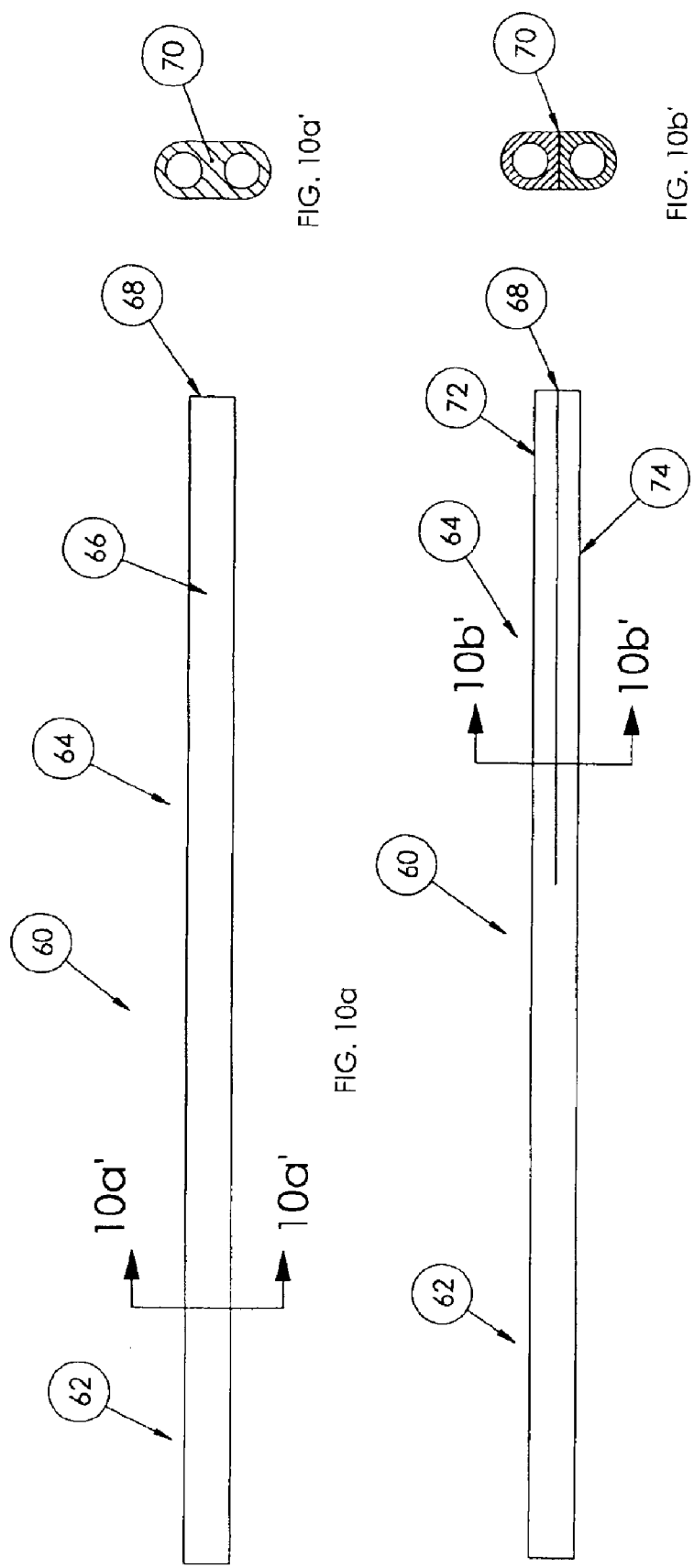

SPLITTABLE MULTILUMEN CATHETER ASSEMBLY

RELATED APPLICATIONS

The present application is a Continuation application of U.S. patent application Ser. No. 10/300,999, filed Nov. 21, 2002, U.S. Pat. No. 6,695,832, which is a Continuation-in-Part application of U.S. patent application Ser. No. 09/585,149, filed Jun. 1, 2000 U.S. Pat. No. 6,719,749, and which also claims the benefit of U.S. Provisional patent application Ser. No. 60/331,882, filed Nov. 21, 2001. Each of the above-referenced related applications are incorporated herein by this reference.

FIELD OF THE INVENTION

The present invention relates generally to multilumen catheter assemblies, and more particularly to multilumen catheter assemblies having a smooth, rounded unitary catheter portion for positioning at a vessel wall insertion site and independent, free floating catheter tubes for positioning within an area to be catheterized.

BACKGROUND OF THE INVENTION

Catheters for the introduction or removal of fluids may be located in various venous locations and cavities throughout the body for the introduction or removal of fluids. Such catheterization may be performed by using a single catheter having multiple lumens. A typical example of a multiple lumen catheter is a dual lumen catheter in which one lumen introduces fluids and one lumen removes fluids. Catheterization may also be performed by using separate, single lumen catheters inserted through two different incisions into an area to be catheterized. Such multiple catheter assemblies are known as Tesio catheters. Procedures are also known, as described in U.S. Pat. No. 5,624,413 for inserting two wholly independent single lumen catheters into a vessel through a single insertion site.

Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through a syringe needle or other introducer device, into the interior of the vessel. The introducer device is then removed leaving the guide wire within the vessel. The guide wire projects beyond the surface of the skin.

At this point, several options are available to a physician for catheter placement. The simplest is to pass a catheter into the vessel directly over the guide wire. The guide wire is then removed leaving the catheter in position within the vessel. However, this technique is only possible in cases where the catheter is of a relatively small diameter, made of a stiff material and not significantly larger than the guide wire, for example, for insertion of small diameter dual lumen catheters. If the catheter to be inserted is significantly larger than the guide wire, a dilator device is first passed over the guide wire to enlarge the hole. The catheter is then passed over the guide wire, and the guide wire and dilator are removed.

In the case of an individual, single-lumen catheter typically used in multiple catheter assemblies (e.g., a Tesio catheter), a physician may use an introducer sheath. If a Tesio catheter is used for hemodialysis, for example, each catheter is inserted in two separate veins, such as the femoral vein. Alternatively, each catheter may be inserted in two different locations of the same vein, such as the internal jugular vein as noted above. The introducer sheath is simply a large, stiff thin-walled tube, which serves as a temporary conduit for the permanent catheter which is being placed. Tearaway sheaths are also available which split apart for easier removal. The introducer sheath is positioned by placing a dilator device inside of the introducer and passing both the dilator and the introducer together into the vessel over a guide wire. The guide wire, left in the vessel after insertion as described above, and the dilator are then removed, leaving the thin-walled introducer sheath in place. The catheter is placed through the introducer sheath. Each of the catheters in the assembly is typically subcutaneously secured within the patient's body by a cuff located in a subcutaneous tunnel, or by otherwise externally affixing the catheter to the body.

The Tesio catheter may also be inserted, in accordance with the technique described in U.S. Pat. No. 5,624,413, as noted above, through a single insertion point using a sheath into the vessel. The Tesio catheter, once inserted in the vessel, is then tunneled separately through the patient in two subcutaneous tunnels for securement of the external, proximal portions of the catheter.

The Tesio double catheter assembly, while comfortable for the patient, due to its soft durometer, and very effective for hemodialysis, typically requires multiple procedures and incisions for insertion and/or for tunneling, which increase the attendant risks of the catheterization procedure. Further, in the case of side-by-side placement of two catheter tubes through a single insertion site in a vessel, while minimizing the number of procedures, can present a potential for leakage between the catheter tubes at the point where the catheter tubes pass into the vessel.

However, Tesio catheter assemblies provide catheters which are capable of independent movement within the vessel. Such catheters present several advantages over unitary multilumen catheters formed of a single internally divided tube when in the vessel. Because the individual tubes of a Tesio double catheter assembly are independently movable at their fluid outlets, it is possible to provide fluid intake and/or return flow around the entire circumference of the distal ends of the catheter tubes. In addition, if one tube becomes blocked, or otherwise requires replacement, it can be removed independently of the other tube. Further, the softer durometer of such catheters, which are typically made of a silicone or a similar material, reduces the risk of vessel wall damage. The 360° circumferential flow provides a more stable tube within the vessel, which is less likely to be suctioned against the vessel wall due to a pressure differential, as occasionally occurs in the use of some side-by-side multi-lumen catheters.

U.S. Pat. No. 5,718,692, issued to Schon, et al., ("the Schon catheter") describes a self-retaining double catheter system in which each catheter can be subcutaneously secured without the use of fabric tissue ingrowth cuffs or external suturing as a result of the placement of a retaining sleeve surrounding both individual catheters in a multiple catheter assembly to hold the catheters together at the location of the sleeve. The individual catheters are permanently linked in one portion by a hub for self-anchoring under the skin, as an alternative to requiring a fabric stabilizing cuff, such that such cuffs are optional. The distal ends are longitudinally prespaced by an appropriate distance to avoid recirculation. While this device requires only one incision, it requires two subcutaneous tunnels in order to facilitate the self-retaining feature. This catheter provides independently movable distal ends within the vessel and 360° circumferential flow in the manner of a standard Tesio. Further, since the retaining sleeve is located outside the vessel when in place to provide the self-retaining feature, at the point of entry into the vessel, the catheters are side-by-side in the manner of a standard Tesio catheter, and there still remains the potential risk of blood leakage between the catheters at the vessel site.

U.S. Pat. No. 5,947,953 discloses a splittable multiple catheter assembly that has a hub and at least two fully independent catheter tubes which are initially releasably joined together, for example, by a breakable membrane. A single subcutaneous tunnel may be used in inserting the catheter, and the catheter tubes are at least partially separated by splitting the catheter tubes prior to insertion into a vessel. As a result, the portions of the catheter within the vessel are capable of independently moving and having 360° circumferential flow from the distal portion of each tube. The catheter may be secured using standard securement means such as suturing, ingrowth or other available securement devices.

A further multiple catheter assembly is described in U.S. Pat. No. 5,776,111 for use in acute Tesio catheterizations. The assembly includes two independent single lumen catheters joined at a location by a generally flat disc that may be attached to the surface of a patient's skin to secure the assembly in an acute procedure. The distal ends are prespaced to avoid recirculation.

There is a need in the art for a multiple catheter assembly and a need for making such a catheter assembly which can provide the advantages of the above-mentioned multi-lumen catheters with respect to easy insertion through a single tunneling procedure and which can prevent the potential risk of leakage at the site of vessel entry, but which can still provide the advantage of multiple catheter assemblies with respect to independent movement within a vessel and good flow properties.

SUMMARY OF THE INVENTION

The present invention is a multilumen catheter assembly which provides easy catheter insertion by a single tunneling procedure and assists the prevention of leakage at the site of vessel entry through use of a unitary, outer wall configuration. The catheter assembly also provides independent, free floating movement within the vessel through use of separate, distal end catheter tubes and provides efficient fluid flow properties within lumens of the catheter assembly.

In one aspect of the present invention, the multilumen catheter assembly includes a unitary portion having an outer wall, a distal end, a proximal end, and a plurality of lumens extending longitudinally through the unitary portion. In this aspect, the catheter assembly also includes a plurality of distal end tubes, each defining a longitudinally extending lumen therethrough, where the lumens of the distal end tubes are each in fluid communication with a respective lumen of the unitary portion, and the distal end tubes are capable of independent movement with respect to each other. In this aspect of the invention, the outer wall of the unitary portion, the outer wall of the distal end tubes, and the lumens, can have various shapes in cross section, such as but not limited to a circular, semi-circular, or oval shape. The unitary portion, the distal end tubes, and the lumens, can also have a different shape or configuration at different points along a respective longitudinal length of each.

In another aspect of the present invention, the multilumen catheter assembly includes a unitary catheter having an rounded exterior surface, a first lumen and a second lumen extending longitudinally therethrough, a distal end and a proximal end; and a first distal end tube defining a first longitudinally extending passageway and a second distal end tube defining a second longitudinally extending passageway, where the first and the second distal end tubes extend distally from the distal end of the unitary catheter, the first passageway in the first distal end tube being in fluid communication with the first lumen, the second passageway in the second distal end tube being in fluid communication with the second lumen and the first and second distal end tubes are capable of independent movement with respect to each other.

In another aspect of the present invention, the distal end tubes are releasably attached to one another over a portion, or the entirety, of their longitudinal length, allowing the first and the second distal end tubes to be split, through use of minimal force, and separate over any portion of their longitudinal length.

In another aspect of the present invention, the first and the second distal end tubes are releasably attached to one another, and possibly having an outer wall with semi-circular cross section, from the distal end of the unitary catheter to a bonding point located between the distal end of the unitary catheter and the distal end of the catheter assembly, allowing the first and the second distal end tubes to be split, through use of minimal force, to any longitudinal point between the distal end of the unitary catheter and the transition point, the first and the second distal end tubes being separate from one another, and possibly circular in cross section, from the transition point to the distal end of the catheter assembly, providing the first and the second distal end tubes with individual and independent movement with respect to each other from the transition point to the distal end of the catheter assembly. In this aspect of the present invention, the unitary catheter can have a generally oval cross section.

In another aspect of the invention, the multilumen catheter assembly includes two catheter tubes, each having a round lumen extending longitudinally therethrough and each having an exterior of generally semi-circular cross sectional shape. In this aspect, the catheter assembly also includes a hub securing the two catheter tubes in juxtaposed alignment with respect to one another, wherein the tubes in juxtaposed alignment together have a generally oval shape in cross section.

The present invention also provides a method for making a multilumen catheter assembly, the method includes forming a unitary catheter tube having a proximal portion and a distal portion, the distal portion terminating at a distal end and the proximal portion terminating at a proximal end, the unitary catheter tube having a first lumen and a second lumen, the first lumen and the second lumen each extending longitudinally through the unitary catheter tube. The formed unitary catheter tube is then split longitudinally along the distal portion to form a first distal end tube and a second distal end tube. The unitary catheter tube, the distal end tubes, and lumens within each, can each then be finished, if desired, to have one or more configurations, or cross sectional shapes, over a respective longitudinal length of each.

In one aspect of the present invention, the distal end tubes are then releasably attached along any portion, or an entirety, of their longitudinal lengths. In another aspect, the distal end tubes are releasably attached from a transition point (the point of transition, after splitting, between the unitary catheter and the first and the second distal end tubes) to a bonding point located between the transition point and the distal end of the catheter assembly.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings certain embodiments of the present invention. It should be understood, however, that the invention is not limited to the precise arrangements and instrumentalities shown. In the drawings, the same reference numerals are employed for designating the same elements throughout the several figures. In the drawings:

FIG. 1 is a top view of a multilumen catheter assembly in accordance with a first embodiment of the present invention;

FIGS. 1a and 1b are enlarged cross-sectional views of the multilumen catheter assembly of FIG. 1 taken along lines 1a—1a and 1b—1b, respectively;

FIGS. 2a through 2e are enlarged cross-sectional views of alternative embodiments of the multilumen catheter assembly of FIG. 1 taken along line 1b—1b;

FIG. 2f is an enlarged cross-sectional view of an alternative embodiment of the multilumen catheter assembly of FIG. 1 taken along line 1a—1a;

FIG. 4 is a top view of a multilumen catheter assembly in accordance with a second embodiment of the present invention;

FIGS. 4a, 4b and 4c are enlarged cross-sectional views of the multilumen catheter assembly of FIG. 4 taken along lines 4a—4a, 4b—4b, and 4c—4c, respectively;

FIG. 5 is a top view of a multilumen catheter assembly in accordance with a third embodiment of the present invention;

FIGS. 5a and 5b are enlarged cross-sectional views of the multilumen catheter assembly of FIG. 5 taken along lines 5a—5a and 5b—5b, respectively;

FIG. 6 is a top view of a multilumen catheter assembly in accordance with a fourth embodiment of the present invention;

FIGS. 6a and 6b are enlarged cross-sectional views of the multilumen catheter assembly of FIG. 6 taken along lines 6a—6a and 6b—6b, respectively;

FIG. 7 is a top view of a multilumen catheter assembly in accordance with a fifth embodiment of the present invention;

FIGS. 7a and 7b are enlarged cross-sectional views of the multilumen catheter assembly of FIG. 7 taken along lines 7a—7a and 7b—7b, respectively;

FIG. 8 is a top view of a multilumen catheter assembly in accordance with a sixth embodiment of the present invention;

FIGS. 8a and 8b are enlarged cross-sectional views of the multilumen catheter assembly of FIG. 8 taken along lines 8a—8a and 8b—8b, respectively;

FIG. 9 is a top view of a multilumen catheter assembly in accordance with a seventh embodiment of the present invention;

FIGS. 9a and 9b are enlarged cross-sectional views of the multilumen catheter assembly of FIG. 9 taken along lines 9a—9a and 9b—9b, respectively;

FIG. 10a is a top view of a unitary catheter tube for use in making a multilumen catheter assembly according to one embodiment of the invention;

FIG. 10a' is an enlarged cross-sectional view of the unitary catheter tube of FIG. 10a taken along line 10a'—10a';

FIG. 10b is a top view of the unitary catheter tube of FIG. 10a which has been split at a distal end to form distal end tubes; and FIG. 10b' is an enlarged cross-sectional view of the unitary catheter tube of FIG. 10b taken along line 10b'—10b'.

DETAILED DESCRIPTION OF THE INVENTION

Figure 3:
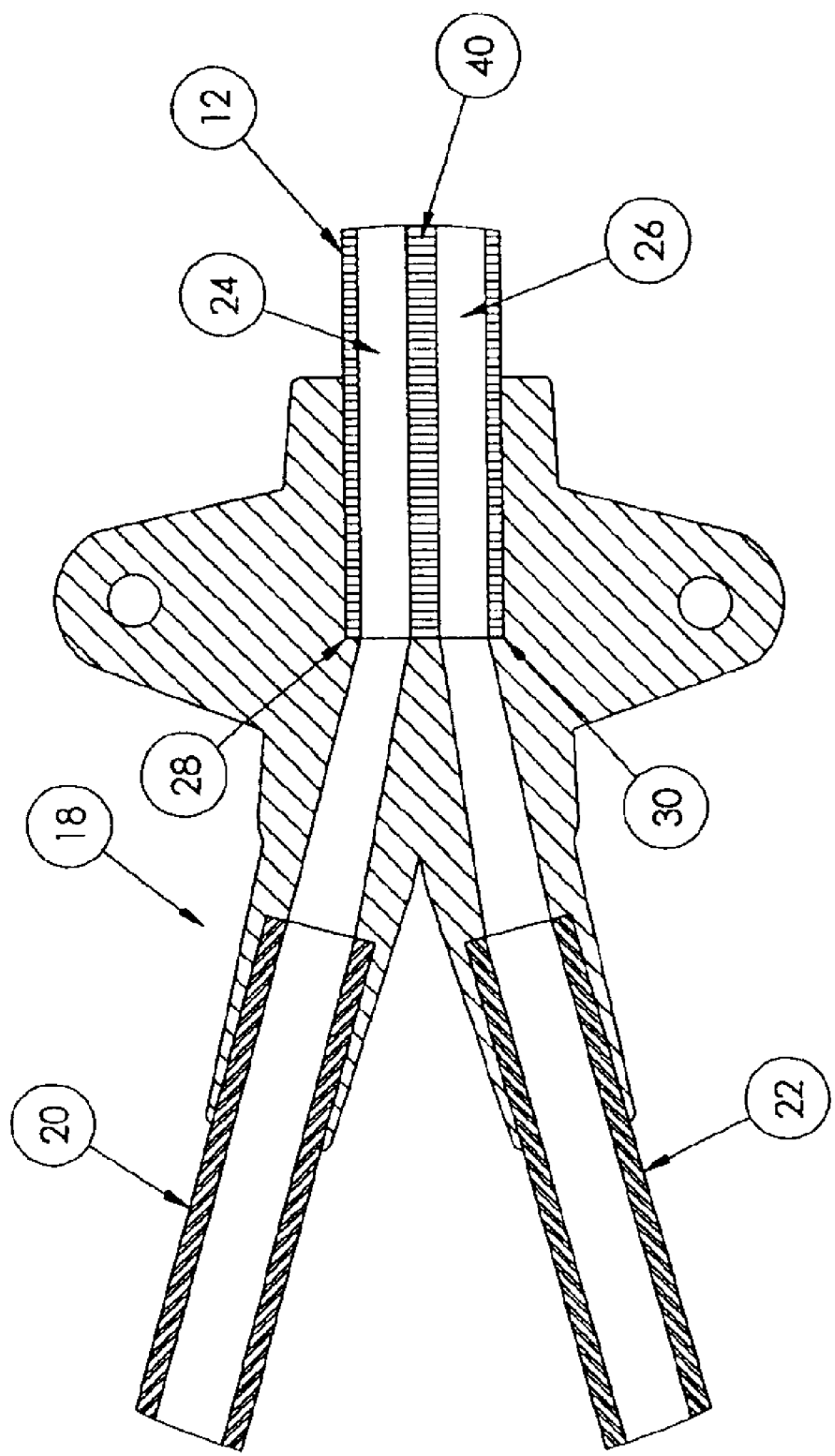
FIG. 3 is an enlarged cross-sectional view of the hub of the multilumen catheter assembly of FIG. 1.

In describing the embodiments of the invention illustrated in the drawings, specific terminology will be used for the sake of clarity. However, the invention is not intended to be limited to the specific terms so selected, it being understood that each specific term includes all technical equivalents operating in similar manner to accomplish similar purpose. It is understood that the drawings are not drawn exactly to scale. In the drawings, similar reference numbers are used for designating similar elements throughout the several figures.

The following describes particular embodiments of the invention. However, it should be understood, based on this disclosure, that the invention is not limited to the embodiments detailed herein. Generally, the following disclosure refers to double lumen catheter assemblies, although catheter assemblies having three or more lumens and/or distal end tubes are within the scope of the invention. Further, the methods described below for making the catheter assemblies of the present invention are also applicable to making catheter assemblies having more than two lumens and/or distal end tubes. It is only for reasons of convenience that the following description refers to two lumen embodiments of the present invention.

The multilumen catheter assemblies of the present invention are inserted into an area of a body of a patient to be catheterized for removing and introducing fluids to the body. The catheter assemblies of the present invention are secured to a fixed location in or on the patient body, such as a subcutaneous area, before the catheter assembly is properly inserted and positioned in the area to be catheterized. This method is particularly preferred for chronic catheterization. Alternatively, in an acute catheterization, the catheter assemblies of the present invention may be secured to an external surface of the body before or after the catheter assembly is properly inserted and positioned in the area to be catheterized.

The multilumen catheter assemblies of the present invention can be adapted for use in various applications in which bodily fluids, medicaments, or other solutions are introduced into and removed from the body, such as perfusion, infusion, plasmapheresis, hemodialysis, chemotherapy, and the like. The catheter assemblies of the present invention are particularly suitable for chronic hemodialysis and apheresis. The area to be catheterized is preferably a blood vessel, such as an internal jugular vein, but may be any suitable area within the body. Other areas in which the catheter assemblies may be used include other blood vessels, including the femoral and subclavian veins, any abscess cavity, post-operative cavity, the peritoneal cavity, and other areas of the body including intra-abdominal, sub-diaphragmatic and subhepatic areas. It is understood that the above-referenced areas are exemplary, and that the catheter assemblies of the present invention may be used to remove or introduce fluids to various areas to be catheterized.

The embodiments of the present invention shown in the figures are particularly useful for intake, or removal, of blood to be purified from a blood vessel, such as the internal jugular vein, and introduction of purified blood into the same vessel. The blood can be purified by any suitable hemodialysis apparatus (not shown), attached in communication with lumens of the disclosed catheter assemblies. The catheter assemblies of the present invention may also be used to introduce medication or other fluids, including glucose or saline solutions, into the body.

For purposes of describing the embodiments of the present invention shown in the figures, the catheter assemblies will be described with respect to an application of hemodialysis; more specifically, an application for purifying blood flowing through an internal jugular vein. However, it is understood that the catheter assemblies of the present invention can be configured and adapted, by increasing or decreasing a size (diameter or length) and/or number of distal end tubes and/or lumens in the respective catheter assembly, so that the catheter assembly can be beneficially used for other medical applications in which fluids are introduced into and/or removed from the body.

A First Embodiment

FIG. 1 illustrates one embodiment of the present invention, where a catheter assembly 5 has at least two lumens. The illustration of two lumens is exemplary, and the scope of the invention encompasses catheters having more than two lumens.

The catheter assembly 5 includes a unitary catheter 12, a first distal end tube 14, a second distal end tube 16, a hub 18, and a first and a second extension tube 20, 22. The multi-lumen catheter assembly 5 includes a first lumen 24 and a second lumen 26 extending longitudinally therethrough (see FIGS. 1a and 1b), the first lumen 24 and the second lumen 26 having proximal ends 28, 30, respectively, terminating within the hub 18, and distal ends 32, 34, respectively, terminating at distal ends 32, 34 of the first and the second distal end tubes 14, 16.

The first lumen 24 is continuous with and through the first extension tube 20, and the second lumen 26 is continuous with and through the second extension tube 22, both by connection at the hub 18. The first and the second extension tubes 20, 22 lead to a proximal end of the catheter assembly 5, through which the materials entering and exiting the patient enter and/or exit the catheter assembly 5. The words "proximal" and "distal" refer to directions away from and closer to, respectively, the inserted end of the catheter assembly 5.

An imaginary transition-point 36 exists at a point along a longitudinal length of the first and the second lumens 24, 26. The catheter assembly 5 can be provided (manufactured) so that the first distal end tube 14 and the second distal end tube 16 are splittable (releasably attached) or separate at their respective distal ends 32, 34, and splittable or separate from their distal ends 32, 34 up to the transition-point 36 (over a longitudinal length in FIG. 1 generally denoted by Arrow "B"). Splittable is defined as releasably attached, meaning the first and the second distal end tubes 14, 16 are adhered, bonded, fused, or otherwise attached, so that only minor force is necessary to pull apart, or split, the tubes 14, 16. Minor force could be defined as approximately one to five pounds of force.

The portion of the catheter assembly 5 between the proximal ends 28, 30 of the first and the second lumens 24, 26 and the transition-point 36 includes the unitary catheter 12 (over a longitudinal length in FIG. 1 generally denoted by Arrow "A"). An exterior of the unitary catheter 12 includes a smooth, curved, and generally convex surface without ridges or grooves. Any of various shapes providing a smooth, curved, and generally convex surface without ridges are contemplated in the present invention.

As shown in FIG. 1a, the cross-section of the unitary catheter 12 can be generally oval in shape (outer configuration), FIG. 1a illustrating in cross-section a generally oval shaped outer wall 38, with the first and the second lumens 24, 26 having a circular cross-section (as shown by outer walls 39 of the first and the second lumens 24, 26) and a first and second lumen separating member 40. Another non-limiting example of a unitary catheter 12 cross-section is shown in FIG. 2f. The lumens 24, 26 within either an oval unitary catheter 12 outer wall 38 configuration (such as FIG. 1a), or a more rounded, or even a circular unitary catheter 12 outer wall 38 configuration (such as FIG. 2f), could be any one of various shapes, such as but not limited to circular, semi-circular, oval, triangular, square, elliptical, or kidney-bean shaped.

A cuff 42 can be located at a point along the unitary catheter 12. Cuffs 42 are known in the art and provide a surface onto which internal tissue may adhere to stabilize the catheter assembly 5 within the patient.

The transition-point 36 can be located exactly at a half-way point of the lumens 24, 26 (i.e., at a point half-way between the proximal ends 28, 30 and the distal ends 32, 34 of the lumens 24, 26, the half-way point measured using the longest of the lumens 24, 26 if the lumens 24, 26 are of different lengths, such as in FIG. 1). The transition-point 36, however, could be located at any point along the longitudinal length of the catheter assembly 5. In FIG. 1, for instance, the transition-point 36 is located at the mid-point between the distal end 32 and the proximal end 28 of the first lumen 24.

In another aspect of the invention, the transition-point 36 is located at a point along the longitudinal length of the lumens 24, 26 such that a longitudinal length of the separate or splittable portion of the lumens 24, 26 (i.e., the first and the second distal end tubes 14, 16, as generally denoted by Arrow "B") is greater than a longitudinal length of the unitary catheter 12 (as generally noted by Arrow "A"). In this alternative embodiment, the longitudinal length of the separate or splittable portion of the lumens 24, 26 (the Arrow "B" portion) is measured using the longer of the lumens 24, 26. Alternatively stated, the first and the second lumens 24, 26 are separate or splittable from one another (i.e., releasably attached) from their respective distal ends 32, 34 to a point on the lumens 24, 26 that is at least one-half of the length of the lumens 24, 26 measured from the distal end of the longest lumen to the respective proximal end of the longest lumen.

In the above mentioned embodiments, it is noted that the proximal ends 28, 30 of the lumens 24, 26 may occur at different locations in various catheters. It is within the scope of the present invention to incorporate, in the dimensional aspects of length disclosed above, all locations where the proximal ends 28, 30 could be said to occur in catheters known in the art, disclosed herein, or to be developed.

The smooth, curved, generally convex exterior surface of the unitary catheter 12 passes through and remains positioned at a vessel wall insertion site during insertion of the catheter assembly 5 into a patient. A vessel wall seals quite well around the smooth, curved exterior surface of the unitary catheter 12, as shown in cross-section in FIG. 1a, and seals particularly well with a ligature. Since the exterior of the unitary catheter 12 provides a good seal at the insertion site, the risk of blood loss around the catheter assembly 5 at the insertion site is minimized. This is especially true relative to a situation where individual lumens pass through and remain located at a vessel wall insertion site, as a tight seal around individual lumens having, generally, a figure-8 configuration is difficult (the reference to a figure-8 configuration referring to the exterior cross-section of two, circular and individual lumens, such as that shown in FIG. 1b).

The first and the second distal end tubes 14, 16 extend distally from the unitary catheter 12 at the transition point 36, with the first and the second lumens 24, 26 having continuous fluid communication therethrough. The first and the second distal end tubes 14, 16 preferably have outer surfaces continuous with the outer wall 38 of the unitary catheter 12, and are capable of independent movement when split from one another.

The first and the second distal end tubes 14, 16 can be well known in the art, or newly developed. In FIG. 1b, the first and the second distal end tubes 14, 16 are defined by circular outer walls 44 of the first and the second distal end tubes 14, 16, the first and the second lumens 24, 26, the circular outer walls 39 of the first and the second lumens 24, 26, and a junction point 46. FIGS. 2a through 2e illustrate cross-sections of alternative embodiments of splittable first and second distal end tubes 14, 16 (i.e., alternatives to the FIG. 1b embodiment). The junction point 46 can be created by weak adhesives (FIGS. 2a, 2c, & 2e), by molding (FIG. 2b), by tongue-in-groove arrangement (FIG. 2d), or by other methods enabling the distal end tubes 14, 16 to be split through use of minimal force, such that the juncture of the lumens is not fixed.

The first and the second distal end tubes 14, 16, and the first and the second lumens 24, 26 within the distal end tubes 14, 16, have a generally circular cross section in the FIG. 1 embodiment of the present invention, as shown in FIG. 1b. The first and the second lumens 24, 26 are circular, as shown by the outer walls 39, since circular cross sections are most conducive to fluid flow properties. However, other shapes such as D-shaped passageways and/or lumens (FIG. 2c), oval, triangular, square, elliptical, kidney-bean shaped passageways and/or lumens, or other configurations are also within the scope of the invention (some of which are shown in FIGS. 2a through 2e). Further, while the distal end tubes 14, 16 and the lumens 24, 26 are preferably identical in cross section, it is within the scope of the invention to vary the size, shape and/or configuration of the distal end tubes 14, 16 and/or the lumens 24, 26 such that smaller distal end tubes and/or lumens, or varying types of lumens and distal end tubes may be used for other applications, such as an addition of a third, smaller lumen and corresponding distal end tube for introduction of medication.

FIG. 3 illustrates a cross-section of the hub 18 of FIG. 1, the hub 18 providing a reinforced area for termination of the proximal ends 28, 30 of the first and the second lumens 24, 26, and for termination of distal ends of the extension tubes 20, 22. The hub could also include one or more suture wings for securing the catheter assembly to the body, if desired. Use of other hub configurations, as well as use of a detachable hub, is also envisioned for the present invention.

A Second Embodiment

FIG. 4 illustrates a catheter assembly 6, which is a second embodiment of the present invention, an embodiment having additional limitations relative to the catheter assembly 5 of FIG. 1. The catheter assembly 6 of FIG. 4 is primarily distinguished from the catheter assembly 5 of FIG. 1 over the portion of the catheter assembly 6 between the distal ends 32, 34 and the transition-point 36 (over the portion of the longitudinal length of the catheter assembly 6 generally denoted by Arrow "B" in FIG. 4). In one aspect of the FIG. 4 embodiment, the transition-point 36 is located at a point along the longitudinal length of the lumens 24, 26 such that the length of the longer of the first and the second distal end tubes 14, 16 (the Arrow "B" portion) is greater than the length of the unitary catheter 12 (the Arrow "A" portion).

In the FIG. 4 embodiment, the outer walls 44 of the first and the second distal end tubes 14, 16 are releasably attached from the transition point 36 to an imaginary bonding point 48 (over a longitudinal length generally denoted by Arrow "B1" in FIG. 4). The releasable attachment of the first and the second distal end tubes 14, 16, from the transition point 36 to the bonding point 48 allows the first and the second distal end tubes 14, 16 to be split, through use of minimal force, to any selected longitudinal point between the transition point 36 and the bonding point 48.

Between the transition point 36 and the bonding point 48, the cross section of the first and the second distal end tubes 14, 16 (FIG. 4b) illustrates that the outer configuration of the first and the second distal end tubes 14, 16 over the Arrow "B1" length resembles that of the unitary catheter 12 (i.e., smooth, curved, and generally oval shaped). FIG. 4b also illustrates that the first and the distal end tubes 14, 16, when individually viewed, are semicircular in shape, each have a generally "D" shaped outer wall 44, with a junction point 46 of weak adhesive between the flat side portions of the "D" shaped outer walls 44, the weak adhesive providing splittability through use of minimal force. In FIG. 4b, the flat side portions face each other, and are identical to each other so that a cannulating portion of the catheter assembly 6 retains a rounded, generally oval cross section.

The flat side portions, when placed back to back to provide an overall oval outer configuration for the distal end tubes, assist in preventing blood tracking between the tubes, as no rounded or grooved surfaces exist between the tubes for blood to travel. The flat side portions of the tubes allow the tubes to fit back together (if separate, independent tubes are not desired) as if the tubes were never separated, and are still unitary in configuration.

The catheter assembly 6 includes adhesive, or a splittable membrane, to provide releasable attachment between the tubes 14, 16. The adhesive extends longitudinally between and joins the opposite, generally flat side portions of the first and second distal end tubes 14, 16 (FIG. 4b). The adhesive (not shown in the figures) can extend longitudinally along a central line of the flat side portions of the tubes 14, 16 to provide dimensional stability. However, the adhesive could extend between edges of the flat side portions, or between other regions of the flat side portions, or the rounded wall portions of the tubes 14, 16.

The adhesive, or splittable membrane, performs multiple functions. First, the membrane joins the tubes 14, 16 so that the tubes 14, 16 can be easily manipulated, particularly where the membrane is unbroken. Where the membrane is completely intact, the catheter assembly 6 can be manipulated as a single catheter (e.g., the unitary catheter 12). Second, the membrane allows the first and the second distal end tubes 14, 16 to be at least partially longitudinally split apart from each other, without damaging the outer walls 44 of the tubes 14, 16, to allow independent movement of the split portions in the vessel or other area to be catheterized. The membrane is constructed to split easily when the first and the second tubes 14, 16 are separated from each other, thereby tearing or splitting before the opposing forces exerted on the tubes 14, 16 reach a level sufficient to cause damage thereto. However, the membrane should be sufficiently strong to resist tearing during normal handling of the catheter assembly 5.

From the bonding-point 48, to the distal ends 32, 34 of the first and the second lumens 24, 26, the first and the second distal end tubes 14, 16 are separate (unattached) and independent (over a longitudinal length generally denoted by Arrow "B2" in FIG. 4). In one aspect of the present invention, the cross section of the first and the second distal end tubes 14, 16 (FIG. 4c) illustrates that the outer walls 44 of the first and the second distal end tubes 14, 16 over the Arrow "B2" length are rounded. As shown in FIGS. 4a, 4b, and 4c, the outer walls 39 of the first and the second lumens 24, 26 illustrate a circular cross section for the lumens 24, 26.

A Third Embodiment

FIG. 5 illustrates a catheter assembly 7, which is a third embodiment of the present invention. The catheter assembly 7 of FIG. 5 is primarily distinguished from the catheter assembly 5 of FIG. 1 over the portion of the catheter assembly 7 between the distal ends 32, 34 and the transition-point 36 (over the portion of the longitudinal length of the catheter assembly 7 generally denoted by Arrow "B" in FIG. 5).

In the FIG. 5 embodiment, the outer walls 44 of the first and the second distal end tubes 14, 16 are separate (unattached) and independent from the transition point 36 to the distal ends 32, 34 (over the entire Arrow "B" longitudinal length in FIG. 5), as shown in FIG. 5b. The cross section of the first and the second distal end tubes 14, 16 (FIG. 5b) illustrates that the outer walls 44 of the first and the second distal end tubes 14, 16 over the Arrow "B" length, as well as the outer walls 39 of the first and the second lumens 24, 26, are rounded or circular.

The portion of the catheter assembly 7 between the proximal ends 28, 30 of the first and the second lumens 24, 26 and the transition-point 36 includes the unitary catheter 12 (over a longitudinal length in FIG. 5 generally denoted by Arrow "A"). As in the embodiments of FIGS. 1 and 4, the exterior of the unitary catheter 12 includes a smooth, curved, and generally convex surface. As shown in FIG. 5a, the cross-section of the unitary catheter 12 is generally oval in shape, FIG. 5a illustrating in cross-section the generally oval shaped outer wall 38 of the unitary catheter 12 and the circular shaped outer walls 39 of the first and the second lumens 24, 26.

A Fourth Embodiment

FIG. 6 illustrates a catheter assembly 8, which is a fourth embodiment of the present invention. The catheter assembly 8 of FIG. 6 does not include a distinctive unitary catheter 12 portion, but rather includes the first and the second distal end tubes 14, 16 extending substantially the entire length of the catheter assembly 8 (over the longitudinal length generally denoted by Arrow "B" in FIG. 6). Although the catheter assembly 8 of FIG. 6 does not include a distinctive unitary catheter 12, a proximal portion of the first and the second distal end tubes 14, 16 (through and including termination of the proximal ends of the first and the second distal end tubes 14, 16 within the hub 18) includes an outer configuration having a smooth, rounded, and generally oval shaped perimeter. The hub 18 is similar to that shown in cross section in FIG. 3.

As shown in FIG. 6a, the cross section of the catheter assembly 8 over that portion of its longitudinal length generally denoted by Arrow "A" in FIG. 6, is generally oval in shape, FIG. 6a illustrating the generally oval shaped outer wall 38 and the circular shaped outer walls 39 of the first and the second lumens 24, 26. In the FIG. 6 embodiment of the invention, the cross section of the Arrow "A" portion of the catheter assembly 8 could include a single, oval shaped portion (as shown in FIG. 6a) or two semi-circular ("D" shaped) distal end tubes 14, 16, placed back to back (i.e., with the flat portions of the semi-circle adjoining, as shown in FIGS. 2e and 4b) with the flat portions permanently bonded, with perhaps a suitable adhesive, to one another.

The outer walls 44 of the first and the second distal end tubes 14, 16 can be separate (unattached) and independent over the Arrow "B" portion of the longitudinal length of the catheter assembly 8 of FIG. 6), or the first and the second distal end tubes 14, 16 can be releasably attached (splittable) over this length. In either case, the cross section of the first and the second distal end tubes 14, 16, as shown in FIG. 6b, illustrates that the outer walls 44 of the first and the second distal end tubes 14, 16, as well as the outer walls 39 of the first and the second lumens 24, 26, are rounded or circular.

Further, it is envisioned that the first and the second distal end tubes 14, 16 could have alternative features, such as but not limited to those shown in FIGS. 2a through 2e, or as described above with regard to the first embodiment of the present invention.

A Fifth Embodiment

FIG. 7 illustrates a catheter assembly 9, which is a fifth embodiment of the present invention. The catheter assembly 9 of FIG. 7 is similar to the catheter assembly 8 of FIG. 6, distinguished only by incorporation of an alternative hub 18.

A hub provides a reinforced area for the proximal ends 28, 30 of the first and the second lumens 24, 26, respectively, to communicate with distal ends of extension tubes. The hub also provides a means to secure one or more lumens to one another, thereby limiting capability of the lumens to be separated or to be splittable. Accordingly, the present invention contemplates use of any hub type device accomplishing the above, either known in the art or to be developed, including detachable hub devices.

As known in the art, hubs 18 may be sealed, such as by bonding, adhering, heat molding, or through other attachment, to a distal end of an extension tube (or extender) and a proximal end of a tube or lumen. In one aspect of the invention, extension tubes are proximal portions of two separate lumens which are coated with an outer layer, perhaps by heat molding, to form a unitary body portion of the assembly. Accordingly, the extension tubes are continuous with the proximal ends of the lumens, and the hub 18 can be simply molded or otherwise adhered around the proximal ends of the lumens and around the distal ends of the extension tubes. In another aspect of the invention, the hub 18 (outer layer) is molded or otherwise adhered around some midpoint portion of a first and a second tube or lumen, creating extension tubes and a catheter assembly from one set of tubes or lumens. If either aspect, above, is the embodiment of the hub 18 incorporated into the catheter assembly 9 of FIG. 7, it is understood that the proximal end 28, 30 of the first and the second lumens 24, 26 occurs at the point where the extension tubes 20, 22 diagonally diverge from the hub 18.

A Sixth Embodiment

FIG. 8 illustrates a catheter assembly 10, which is a sixth embodiment of the present invention. The catheter assembly 10 of FIG. 8 is similar to the catheter assembly 8 of FIG. 6, but includes first and second distal end tubes 14, 16 which are separate (unattached) and independent over a substantial length of the catheter assembly 10 (over the entire longitudinal length generally denoted by Arrow "B" in FIG. 8). FIG. 8b illustrates a cross section of the first and the second distal end tubes 14, 16, showing circular outer walls 44 for the first and the second distal end tubes 14, 16, as well as circular outer walls 39 for the first and the second lumens 24, 26.

The catheter assembly 10 of FIG. 8 also includes a proximal portion of the first and the second distal end tubes 14, 16 with an outer configuration having a smooth, rounded, and generally oval shaped perimeter. As shown in FIG. 8a, the cross section of the catheter assembly 10 over the Arrow "A" portion of the longitudinal length is generally oval in shape, FIG. 8a illustrating the generally oval shaped outer wall 38 and the circular shaped outer walls 39 of the first and the second lumens 24, 26. Further, the cross section of the Arrow "A" portion of the catheter assembly 10 could include a single, oval shaped portion (as shown in FIG. 8a) or two semi-circular ("D" shaped) distal end tubes 14, 16, placed back to back (i.e., with the flat portions of the semi-circle adjoining, as shown in FIGS. 2e and 4b) with the flat portions permanently bonded to one another. The hub 18 of the catheter assembly 10 of FIG. 8 is the hub 18 detailed in FIG. 3.

A Seventh Embodiment

FIG. 9 illustrates a catheter assembly 11, which is a seventh embodiment of the present invention. The catheter assembly 11 of FIG. 9 is similar to the catheter assembly 10 of FIG. 8, distinguished only by incorporation of an alternative hub 18. It is envisioned that the present invention could incorporate any hub known in the art, any hub described herein, or any hub to be developed.

General & Alternative Aspects of the Present Invention

The present invention provides aspects of a multiple catheter assembly, having two freely and independently movable distal ends 32, 34, while also providing aspects of a single insertion method and an ability to easily manipulate a proximal portion of the unitary catheter 12 with only one tunneling procedure. The unitary catheter 12, having a smooth, generally convex exterior surface passes easily through an insertion site. A vessel wall can easily seal around the smooth, curved surface of the unitary catheter 12. If round, individual distal end tubes 14, 16 are located at the insertion site, the vessel wall will not seal as easily, or will not be capable of sealing as tightly, as if a single, rounded, generally oval or circular unitary catheter 12 type configuration is used, as a potential risk of leakage exists around and between multiple, rounded distal end tubes due to their "figure-8" configuration.

The releasably attached (i.e., splittable) portion of the catheter assemblies (e.g., the Arrow "B1" portion of FIG. 6, the portion between the transition point 36 and the bonding point 48) provides, for any given patient, further adaptability and flexibility of use and insertion of the respective catheter assembly. The height and weight of the patient each has consequences effecting what a desirable length of a unitary catheter type portion of the catheter assembly would be, in relation to the rest of the catheter assembly, to ensure that a smooth, generally oval cross sectional configuration of the catheter assembly is located at a vessel wall insertion site. The splittable portion of the catheter assembly provides flexibility, at time of catheter assembly insertion, in determining an ideal length of a smooth, generally oval cross section (such as that provided by the unitary catheter configuration of the present invention), and an ideal length of independent (i.e., separate), free floating distal end tubes.

Where releasable attachment using adhesive is employed in the present invention, the outer surfaces of the tubes are reasonably joined using an adhesive having an adhesive strength, relative to the material forming the tubes, greater than the cohesive strength of the adhesive. Since the adhesive is applied as a very thin layer or coating, it is not shown in Figures. However, one of ordinary skill in the art would understand, based on this disclosure, that the adhesive is applied as a partial or complete coating on one or both of the outer walls 44 of the tubes 14, 16 such that when the tubes 14, 16 are pressed together, the outer walls 44 will adhere. As a result of using an adhesive which will adhere more strongly to the tubes then to itself, the adhesive will initially hold the desired portion of the catheter assembly together, allowing manipulation of the catheter assembly in the same manner as a unitary, multi-lumen catheter. However, upon application of opposing transverse forces to distal end portions and/or the distal ends 32, 34, the adhesive will lose cohesive strength and separate longitudinally along the catheter assembly so that the tubes 14, 16 may be at least partially longitudinally split.

The length of the split may be varied depending upon the desired application. For example, for hemodialysis-type applications, in which the catheter assembly is inserted into an area to be catherized, it may be desired to split the tubes 14, 16 only to the extent necessary to facilitate independent movement within the catheterized area. In blood flow and other fluid flow applications, such partial splitting may be desired to avoid the possibility that fluid could escape the catheterized area by passing between the tubes 14, 16 of the catheter assembly. While an adhesive is described herein for providing releasable attachment, it will be understood that other suitable techniques for releasable joining of the tubes 14, 16, such as a breakable ultrasonic weld, or a thin polymeric breakable layer molded between the tubes 14, 16, or other similar structures, could be used without departing from the spirit and scope of the invention, provided the tubes 14, 16 remain splittable longitudinally with only a small amount of manual force. The use of releasable attachment, splittable layers, coatings, adhesives and/or membranes described elsewhere herein, the tubes 14, 16 will not be distorted, stretched or otherwise structurally altered during the splitting of the tubes 14, 16.

The catheter assemblies of the present invention can each have smooth, round distal ends 32, 34, which do not have protuberances on their surfaces that promote clotting. A rough external surface provides protuberances, which can be points where clotting can begin. The distal ends 32, 34, which have smooth, round exterior surfaces that float freely within the vessel, do not provide a source of clot formation. The free-floating distal ends of the present invention provide aspects an individual catheter tube, including no tendency to suction against an inside surface of the vessel wall, which minimizes the tendency of stenosis. The catheter assemblies of the present invention also have little tendency to kink, since the unitary catheter type configuration provides a good deal of support due to a thickness of its walls and cross section, and due to the smoothness of the separate distal end tubes.

As shown in the above-referenced embodiments, the first and the second distal end tubes 14, 16, and the first and the second lumens 24, 26, have a generally circular cross section, since a circular cross section is most conducive to fluid flow properties. However other shapes, such as "D"-shaped, oval, triangular, square, elliptical, kidney-bean shaped, or other configurations, are also within the scope of the invention. Further, while the distal end tubes 14, 16 and the lumens 24, 26 are preferably identical in cross section, it is within the scope of the invention to vary the size, shape or configuration of the distal end tubes and lumens in cross section such that smaller tubes and/or lumens, or varying types of lumens and distal end tubes, may be used for other applications, such as an addition of a third, smaller lumen and corresponding distal end tube for introduction of medication.

It is further within the scope of the invention that the distal end tubes have varying diameters or distal end shapes as are known in the art or to be developed. For example, the distal end tubes may have a larger diameter proximate to the unitary catheter which transitions abruptly or gradually to a smaller diameter proximate to the distal ends of the tubes. Alternatively, a more tapered, conical or angled distal end may be provided for varying applications. However, blunt ends, preferably formed of soft durometer material are preferred for the catheter assembly and distal ends to provide comfort to the patient and to avoid vessel wall trauma and stenosis.

In addition to an end hole 49 at each distal end 32, 34, the first and the second distal end tubes 14, 16 can have a plurality of side holes 50 extending through exterior surfaces of the distal end tubes 14, 16 proximate to the distal ends 32, 34 of the first and the second lumens 24, 26 (as shown in the various figures). The side holes 50 provide additional or alternative flow paths for fluids flowing between an area outside the tubes 14, 16 to an area inside the tubes 14, 16, and vice versa. The side holes 50 can be arranged circumferentially and helically around the distal end tubes 14, 16 to provide optimal flow properties, and to avoid suctioning of the distal tubes 14, 16 against an area to be catheterized, such as a vessel wall. The side holes 50 can be of various shape, but are typically circular or oval, or of some combination thereof.

The side holes 50 may also vary in number between the shorter and longer of the distal end tubes 14, 16. In one aspect of the present invention, the catheter assembly 6 of FIG. 4 includes six side holes 50 in the second distal end tube 16 which spiral on the side facing the first distal end tube 14, and five side holes 50 on the first distal end tube 14, where all side holes 50 are circular except the most proximal hole on the first distal end tube 14, which is oval. In this aspect of the present invention, the side holes 50 are located 60° apart on a 360° spiral.

The side holes 50 minimize vibratory movement of the distal end tubes 14, 16 by equalizing the disturbances of intake and return flow through the side holes 50. Minimizing vibratory movement helps prevent stenosis. The side holes 50 also provide alternative openings in the distal end tubes 14, 16 so that if flow becomes blocked at one or both of the end holes 49 at the distal ends 32, 34, dialysis can continue until a replacement catheter assembly is provided. It is to be understood that the present invention also envisions embodiments having no side holes 50, employing only end holes 49 at the distal ends 32, 34.

Materials Forming the Present Invention

The catheter assemblies of the present invention can be made of biocompatible plastics or elastomers, and preferably made of biocompatible elastomers. Suitable biocompatible plastics may be selected from materials such as polyurethane, polyethylene, homopolymers and copolymers of vinyl acetate such as ethylene vinyl acetate copolymer, polyvinylchlorides, homopolymers and copolymers of acrylates such as polymethylmethacrylate, polymethylmethacrylate, polymethacrylate, ethylene glycol dimethacrylate, ethylene dimethacrylate and hydroxymethyl methacrylate, polyurethanes, polyvinylpyrrolidone, 2-pyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, polyisobutylene, polymethyistyrene and other similar compounds known to those skilled in the art. It should be understood that these possible biocompatible polymers are included above for exemplary purposes and should not be construed as limiting.

If a biocompatible polymeric material is used to form the unitary catheter 12, it is preferred that the distal end tubes 14, 16 and the extension tubes 20, 22 be made of polymeric material, including a polyurethane polymer or a polyolefin polymeric material having a soft durometer, as specified below.

The extension tubes 20, 22 may be made separately from the unitary catheter 12 and the distal end tubes 14, 16, and formed of a material such as polyurethane or a polyvinyl chloride polymer or elastomer. However, it is preferred that the extension tubes 20, 22 are formed of the same material as the unitary catheter 12 and the distal end tubes 14, 16.

It is most preferred to use a biocompatible elastomer for all components of the present invention. Suitable, preferred, biocompatible elastomers for use in forming the unitary catheter 12, the distal end tubes 14, 16, and preferably the extension tubes 20, 22 include biocompatible elastomers such as medical grade silicone rubbers, polyvinyl chloride elastomers, polyolefin homopolymeric and copolymeric elastomers, urethane-based elastomers, and natural rubber or other synthetic rubbers. Preferably, the unitary catheter 12, the distal end tubes 14, 16, and the extension tubes 20, 22 are made of the elastomeric material such that they are flexible, durable, soft, and with respect to those portions inserted in the patient or tunneled, they are easily conformable to the shape of the area to be catheterized and/or the subcutaneous area. Further, these materials help to minimize risk of harm to vessel walls.

If the catheter assemblies of the present invention are used for hemodialysis applications, the unitary catheter 12, the distal end tubes 14, 16, and the extension tubes 20, 22 are most preferably formed of a soft silicone elastomer having a hardness of from about 75-A to about 85-A on a Shore durometer scale. Suitable, preferred elastomers include silicone or polyurethane elastomers, and most preferably polyurethane elastomers, such as, for example, Pelletane® from Dow Corning, or Tecothane®, Carbothane® or Tecoflex®, available from Thermetics.

All components of the present invention may also optionally be made such that they include 20% barium sulfate in the elastomer to provide radiopacity if desired. While it is preferred to have a Shore-A durometer hardness in the above Shore-A durometer range and a somewhat soft material, if a biocompatible elastomer is used, particularly for hemodialysis, it is also possible to use an elastomer having a lower Shore-A durometer hardness outside this range, particularly one of more rigid material if a particular application so requires, without departing from the spirit of the invention. It is also preferred that the hub is formed of an elastomeric material, and most preferably the same material as the remaining components of the catheter. However, the hub, while preferably somewhat flexible, may also preferably be somewhat harder and more rigid, by about 5–10 points on the Shore-A durometer scale, than the other components of the catheter assemblies. It will be understood based on this disclosure that softness or rigidity may be varied for different applications.

In one aspect of the present invention, the unitary catheter 12, the distal end tubes 14, 16, and the extension tubes 20, 22 are all formed of Carbothane® of 85-A durometer. Alternatively, a preferred combination may be formed of a Tecoflex® of durometer of about 80A for the unitary catheter 12 and the distal end tubes 14, 16, and a Pelletane® of durometer of about 80-A for the hub 18 and/or the extension tubes 20, 22. The additional components for attaching to dialysis or similar equipment, including luers, connectors and the like, are preferably formed of a polymeric and/or elastomeric material such as acetal, silicone 80-A or polyvinyl chloride. However, such connectors may be formed from any suitable material known or to be developed in the art for forming such connectors and/or adapters.

Methods of Making the Present Invention

The present invention further includes methods for making the multilumen catheter assemblies described above. Referring now to FIGS. 10a and 10b, the method includes forming a unitary catheter tube 60 having a proximal portion 62, a distal portion 64, and a distal end portion 64 terminating in a distal end tip 66. The unitary catheter tube 60, as shown in FIG. 10a, may be formed using any suitable heat molding process, including injection molding, expansion/compression molding, and extrusion.

In one aspect of the present invention, the unitary catheter tube 60 is formed by extrusion through a die to form internal lumens such as those shown in FIG. 10a'. In this embodiment, the lumens are substantially the same and substantially identical in size and configuration. The unitary catheter tube 60, with internal longitudinally extending lumens, may also be formed by injection molding the tube 60 around metal rods which have the shape of the internal lumens.

Referring now to FIG. 10b, the unitary catheter tube 60 is then split longitudinally along the distal portion 64 of the tube 60 using a sharp edge such as a hot knife or razor blade (not shown) for a pre-determined distance, depending upon the particular size desired for the catheter. In one aspect of the present invention, the unitary catheter tube 60 is split a longitudinal length equal to at least one-half the total length of the tube 60. In another aspect of the present invention, the unitary catheter tube 60 is split a longitudinal length greater than one-half of the total length of the tube 60.

The tube 60 is preferably split as evenly as possible between the two lumens along an internal septum 70 (as shown in FIGS. 10b and 10b'). If more than two lumens are present in the catheter assembly, the unitary catheter tube would be split equally along each internal septum, with preferably a substantially equal amount of tubing material surrounding each of the split portions of the tube.

Splitting the unitary catheter tube 60 forms a first distal end tube 72 and a second distal end tube 74. The second distal end tube 74 can then cut to size relative to the first distal end tube 72, if it is desired that one distal end tube be greater in length than the other. Separate lengths for the distal end tubes helps avoid recirculation of fluids entering and leaving the tubes within the area to be catheterized.

After the unitary catheter tube 60 and the distal end tubes 72, 74 are formed, the exterior surface of the unitary catheter tube 60 and the exterior surfaces of the distal end tubes 72, 74 are then ground and polished to a smooth surface. Radio frequency (RF) tipping can be used to provide the smooth surface. Radio frequency (RF) tipping uses RF energy to re-heat an outer surface until there is some melting and then to polish the surface.

Further, the unitary catheter tube 60 and the distal end tubes 72, 74 could undergo radio frequency (RF) tipping on a mandrel, so that the tubes may be re-shaped to have a generally circular transverse cross section both in the interior passageways (lumens) and on the exterior surfaces, if desired. In one aspect of the invention (referring to FIG. 1), the exterior surface of the distal end tubes are rounded to a circular cross section from the transition point 36 to the distal ends 32, 34 (the Arrow "B" portion). In another aspect of the invention (referring to FIG. 4), the exterior surface of the distal end tubes are rounded to a circular cross section from the bonding point 48 to the distal ends 32, 34 (the Arrow "B2" portion).

Once the surfaces are shaped and smoothed, holes can then be formed in the distal end tubes, if desired, using techniques well known in the art. The number, size, shape, and spacing of the holes are as individually preferred, but some general and specific aspects have been described above.

Portions of the split catheter can now be releasably attached, if desired, by bonding portions of exterior surfaces of the distal end tubes with a weak adhesive. In one aspect of the invention (referring to FIG. 1), portions of the exterior surfaces of the distal end tubes can be adhered (releasably attached) over a proximal part of, or the entirety of, the Arrow "B" portion of the catheter assembly 5 (i.e., over a length beginning at the transition point 36 and extending toward to the distal ends 32, 34, or over an entirety of the length beginning at the transition point 36 and extending to the distal ends 32, 34). In another aspect of the invention (referring to FIG. 4), portions of the exterior surfaces of the distal end tubes are adhered (releasably attached) over an entirety of the length of the tubes beginning at the transition point 36 and extending to the bonding point 48 (the Arrow "B1" portion).

As an alternative to splitting the unitary catheter tube 60, after forming the tube 60, individual distal end tubes, which may be previously extruded or heat molded, may be fused onto the unitary catheter tube 60. The distal end tubes are formed such that they each have a respective longitudinal passageway (lumen) extending longitudinally therethrough, and may also be formed to include a plurality of holes either prior to attachment to the distal end of the unitary catheter tube 60, or after attachment to the unitary catheter tube 60. The distal end tubes can be variously shaped in cross section, as desired, with some general and specific aspects having been described above.

Each formed distal end tube is then attached to the distal end of the unitary catheter tube 60 by a suitable heat molding process, or by another form of attachment, such as adhesive, ultrasonic welding or other methods known in the art, such that the first passageway in the first distal end tube is in fluid communication with the first lumen of the unitary catheter tube and the second passageway in the second distal end tube is in fluid communication with the second lumen in the unitary catheter tube. In one aspect of the present invention, heat fusing is used to attach the distal end tubes, and the fusing may be carried out using heat applied to the unitary catheter tube and to the distal end tubing lengths in a female cavity mold to create a smooth fused portion where the tube and end tube lengths meet.

Making the catheter assembly 6 of FIG. 4 would require a slightly modified process if employing a fusion of individual distal end tubes to a unitary catheter tube. The unitary catheter tube 60 with an exterior having an oval cross section could still be split, prior to fusing round distal end tubes to the distal end of the split unitary catheter tube, as that portion of the catheter assembly 6 of FIG. 4 between the transition point 36 and the bonding point 48 (the Arrow "B1" portion) has an exterior having two semi-circular (double "D") cross sections, as shown in FIG. 4b. Therefore, prior to fusing individual distal end tubes to the distal end of the unitary catheter tube, the unitary catheter tube would require cutting (splitting), as described above, over that distance desired for the Arrow "B1" portion of the catheter assembly 6. Alternatively, performing two fusings of tubes of different cross sections is possible, as is fusing one tube and then grinding and polishing a portion thereof, as described above.

Generally, the extension tubes 20, 22 may be provided either by extruding or molding the extension tubes initially when forming the unitary catheter tube 60 using techniques similar to those used to form the distal end tubes as described above. However, it is preferred to attach the extension tubes to a proximal end of the unitary catheter tube using a hub.

Another alternative to the methods described above for making the present invention includes arranging a first catheter tube and a second catheter tube in a substantially longitudinally parallel arrangement, preferably such that they are juxtaposed to each other, however, a gap may be present between the catheter tubes. Further, more than two catheter tubes may be used and similarly arranged. Each of the catheter tubes is preferably a single lumen catheter, however, multilumen catheters may also be used for some applications. The first and the second catheter tubes each have a respective distal end, distal end portion, and at least one lumen in each catheter tube which extends longitudinally therethrough.

An outer layer (sheet) is formed around at least a portion of the length of the exterior surfaces of the first and second catheter tubes proximal to the distal end portions of the catheters. The outer layer is preferably extruded around the catheter tubes. However, the arrangement of catheter tubes and formation of the outer layer may also be formed by extruding the catheter tubes simultaneously through dies while co-extruding the outer layer around the catheter tubes. However, the outer layer is co-extruded only over a portion of the length of the exterior surfaces of the catheter tubes proximal to the distal end portions.

Once the outer layer is formed, sufficient heat molding capability may be applied to heat mold the first and the second catheter tubes together. The lumens/passageways within the catheter tubes are generally longitudinally parallel, and the catheter tubes are heat molded together in juxtaposed relation and are fixed within the outer layer.

The distal end portions of the catheter tubes extend outwardly and distally from the portions of the lengths of the exterior surfaces of the first and the second catheter tubes which are within the outer layer. Since the distal end portions are not connected, they are capable of free floating, independent movement. It is also within the scope of the invention to heat mold a fill material between the first and the second catheter tubes to ensure that a smooth, oval exterior surface is formed around the catheters once the outer layer is formed.

As previously described, extension tubes may be provided to the ends of the catheter tubes if the outer layer is formed to extend to the proximal ends of the catheter tubes. Alternatively, the outer layer can be formed over only a portion of the length of the catheter tubes, leaving separate and independent proximal ends extending from the area within the outer layer to form extension tubes. In this instance, the proximal end portions serving as extension tubes, in the manner of extension tubes 20, 22 shown in FIG. 1, extend proximally from a proximal end of the outer layer formed around the catheter tubes to provide the unitary catheter 12 of FIG. 1.

A hub is then molded around the proximal end of the outer layer and the distal end of the proximally extending catheter tubes adjacent to the outer layer. Preferably, to maintain the unitary catheter and extension tubes in place, the hub mold either has cavities to receive the tubes, or metal rods inserted through the extension tubes and lumens within the formed unitary catheter portion, to retain the shape of the lumens and hold the tubes in place. A plurality of holes may also be provided to the distal end portions of the catheter tubes.

It will be appreciated by those skilled in the art that changes can be made to the embodiments described above without departing from the broad inventive concept thereof. It is understood, therefore, that this invention is not limited to the particular embodiments enclosed, but is intended to cover modifications within the sphere and scope of the present invention as defined by the intended claims.

What is claimed is:

1. A multilumen catheter assembly comprising:
   a unitary catheter body having:
      a proximal end;
      a distal end;
      a plurality of lumens disposed between the proximal end and the distal end; and
      a longitudinal plane generally bisecting the unitary catheter body,
   wherein the plurality of lumens comprises:
      a first lumen disposed on a first side of the longitudinal plane, wherein the first lumen includes a first distal end tube, wherein the first distal end tube includes at least one of a tongue and a groove disposed proximate to the longitudinal plane; and
   a second lumen disposed on a second side of the longitudinal plane, wherein the second lumen includes a second distal end tube, wherein the second distal end tube includes at least the other of the tongue and the groove disposed proximate to the longitudinal plane;
   wherein each of the at least one tongue is disposable across the longitudinal plane into a respective at least one groove and wherein the first and second distal end tubes are splittable along the longitudinal plane from each other by removing at least a portion of each of the at least one tongue from at least a portion of each of the at least one groove.

2. The multilumen catheter assembly according to claim 1, wherein the first lumen includes a generally flat first face and wherein the second lumen includes a generally flat second face juxtaposed across the longitudinal plane from the first face.

3. The multilumen catheter assembly according to claim 2, wherein the at least one tongue extends from one of the first face and the second face, and wherein the at least one grove extends into the other of the first face and the second face.

4. The multilumen catheter assembly according to claim 1, wherein the first distal end tube comprises a first passageway in fluid communication with the first lumen and wherein the second end tube comprises a second passageway in fluid communication with the second lumen.

5. The multilumen catheter assembly according to claim 4, further comprising a plurality of holes formed through each of the first and second distal end tubes to provide fluid flow from outside the first and second distal end tubes into the first and second passageways, respectively, in the first and second distal end tubes.

6. The multilumen catheter assembly according to claim 1, further comprising a first extension tube in fluid communication with a proximal end of the first lumen and a second extension tube in fluid communication with a proximal end of the second lumen.

7. The multilumen catheter assembly according to claim 6, further comprising a connector and a clamp releasably attached to each extension tube.

8. The multilumen catheter assembly according to claim 1, further comprising a first distal end opening in the first distal end tube and a second distal end opening in the second distal end tube.

9. The multilumen catheter assembly of claim 1, wherein the first and the second distal end tubes each have an exterior generally "D"-shaped in cross section, the "D"-shape defining a generally flat exterior portion and a rounded exterior portion.

10. The multilumen catheter assembly of claim 9, wherein the first and the second distal end tubes are adjoined to one another along their respective flat exterior portions for at least a portion of their longitudinal length.

11. The multilumen catheter assembly of claim 10, wherein the adjoined first and second distal end tubes together have an exterior that is generally round in cross section.

12. The multilumen catheter assembly of claim 1, wherein the splittable portion of the first and the second distal end tubes are releasable through use of minimal force.

13. The multilumen catheter assembly of claim 12, wherein the minimal force is between five pounds of force.

14. The multilumen catheter assembly of claim 1, wherein the first lumen has a first passageway having a generally circular cross section and wherein the second lumen has a second passageway having a generally circular cross section.

* * * * *

UNITED STATES PATENT AND TRADEMARK OFFICE
CERTIFICATE OF CORRECTION

PATENT NO.       : 7,018,374 B2
APPLICATION NO. : 10/659824
DATED            : March 28, 2006
INVENTOR(S)      : Donald A. Schon, Anthony J. Madison and Timothy M. Schweikert It is certified that error appears in the above-identified patent and that said Letters Patent is hereby corrected as shown below:

On the title page, item [73] should read:
(73) Assignee: TwinCath, LLC
               Paradise Valley, AZ (US)

Medical Components, Inc.
               Harleysville, PA (US)

Signed and Sealed this

Sixth Day of February, 2007

JON W. DUDAS
*Director of the United States Patent and Trademark Office*